US010654790B2

(12) United States Patent
Kouba et al.

(10) Patent No.: US 10,654,790 B2
(45) Date of Patent: May 19, 2020

(54) RECOVERY PROCESS FOR FUNCTIONALIZED COMPOUND REACTION PRODUCT

(71) Applicant: The Scripps Research Institute, La Jolla, CA (US)

(72) Inventors: Jay Kouba, La Jolla, CA (US); Stephen Pietsch, Dublin, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/506,611

(22) PCT Filed: Aug. 26, 2015

(86) PCT No.: PCT/US2015/046935
§ 371 (c)(1),
(2) Date: Feb. 24, 2017

(87) PCT Pub. No.: WO2016/033174
PCT Pub. Date: Mar. 3, 2016

(65) Prior Publication Data
US 2018/0037532 A1    Feb. 8, 2018

Related U.S. Application Data

(60) Provisional application No. 62/042,099, filed on Aug. 26, 2014.

(51) Int. Cl.
| | | |
|---|---|---|
| *C07C 67/035* | (2006.01) | |
| *C07C 67/03* | (2006.01) | |
| *C07C 31/20* | (2006.01) | |
| *C07C 29/48* | (2006.01) | |
| *C07C 67/54* | (2006.01) | |
| *C07C 67/58* | (2006.01) | |
| *C07C 67/04* | (2006.01) | |
| *C07C 51/16* | (2006.01) | |
| *C07C 51/48* | (2006.01) | |
| *C07C 27/16* | (2006.01) | |
| *C07C 45/27* | (2006.01) | |
| *C07C 27/34* | (2006.01) | |
| *C07C 37/60* | (2006.01) | |
| *C07C 45/80* | (2006.01) | |
| *C07C 37/58* | (2006.01) | |
| *C07C 29/86* | (2006.01) | |
| *C07C 69/16* | (2006.01) | |

(52) U.S. Cl.
CPC ............ *C07C 67/035* (2013.01); *C07C 27/16* (2013.01); *C07C 27/34* (2013.01); *C07C 29/48* (2013.01); *C07C 29/86* (2013.01); *C07C 31/205* (2013.01); *C07C 37/58* (2013.01); *C07C 37/60* (2013.01); *C07C 45/27* (2013.01); *C07C 45/80* (2013.01); *C07C 51/16* (2013.01); *C07C 51/48* (2013.01); *C07C 67/03* (2013.01); *C07C 67/04* (2013.01); *C07C 67/54* (2013.01); *C07C 67/58* (2013.01); *C07C 69/16* (2013.01)

(58) Field of Classification Search
None
See application file for complete search history.

(56) References Cited

U.S. PATENT DOCUMENTS

| | | | |
|---|---|---|---|
| 3,950,440 A | 4/1976 | Hirose et al. | |
| 4,203,927 A | 5/1980 | Stapp | |
| 4,237,331 A | 12/1980 | Stapp | |
| 2016/0145188 A1* | 5/2016 | Gunnoe | ............... C07C 67/035 560/192 |

FOREIGN PATENT DOCUMENTS

| | | |
|---|---|---|
| WO | WO 2008/003934 A2 | 1/2008 |
| WO | WO 2009/091913 A1 | 7/2009 |

OTHER PUBLICATIONS

Phenomenex Solvent Miscibility Table (downloaded from https://erowid.org/archive/rhodium/pdf/solvent.miscibility.pdf on Apr. 30, 2018).*
Muller "Liquid-Liquid Extraction" Ullmann's Encyclopedia of Industrial Chemistry, p. 251-307, 2012).*
Leonard ("Chapter 10: Working up the reaction" Advanced Practical Organic Chemistry, 2010, p. 191-208).*
UT ("Chapter 21: Amines", downloaded from http://research.cm.utexas.edu/nbauld/CHAPTER%2021.htm on May 15, 2018, p. 1-13).*
Dodecane (Entry for Dodecane in "Aqueous Solubility and Henry's Law Constants for Organic Compounds", in "Physical Constants of Organic Compounds," CRC Handbook of Chemistry and Physics, 99th Edition (Internet Version 2018), John R. Rumble, ed., CRC Press/Taylor & Francis, Boca Raton, FL., p. 35 (Year: 2018).*
SciFinder entry for 76-05-1 ("2,2,2-trifluoroacetic acid") downloaded from SciFinder on Jan. 4, 2019. (Year: 2019).*
SciFinder entry for 58652-54-3 ("acetic acid, 2,2,2-trifluoro-, tricyclo[3.3.1.13,7]dec-1-yl ester"), downloaded from SciFinder on Jan. 4, 2019 (Year: 2019).*
SciFinder entry for Water (7732-18-5, downloaded from SciFinder on Jan. 4, 2019) (Year: 2019).*

(Continued)

*Primary Examiner* — Amy C Bonaparte
(74) *Attorney, Agent, or Firm* — Leydig, Voit & Mayer, Ltd.

(57) ABSTRACT

Provided is a process for recovery of a functionalized compound reaction product comprising contacting (i) an oxidizing electrophile comprising a main group element, and (ii) a compound comprising at least one C—H bond, in an acidic medium to form a reaction milieu comprising a functionalized compound reaction product, contacting the reaction milieu with a water-immiscible organic solvent, separating the water-immiscible organic solvent from the reaction milieu, wherein the functionalized compound reaction product is dissolved in the water-immiscible organic solvent, and separating the functionalized compound reaction product and the water-immiscible organic solvent. The water-immiscible extraction solvent can be the same compound as the compound comprising as least one C—H bond, for example, propane or n-butane.

19 Claims, No Drawings

(56) References Cited

OTHER PUBLICATIONS

Tripathi "Trifluoroacetic acid Recovery from Industrial Aqueous Effluent" IOSR Journal of Applied Chemistry, vol. 9, issue 11, 2015, p. 70-72 (Year: 2015).*
European Patent Office, International Search Report and the Written Opinion in International Application No. PCT/US2015/046935 (dated Nov. 5, 2015).

* cited by examiner

RECOVERY PROCESS FOR FUNCTIONALIZED COMPOUND REACTION PRODUCT

CROSS-REFERENCE TO RELATED APPLICATIONS

This patent application is a U.S. national phase of International Patent Application No. PCT/US2015/046935, filed Aug. 26, 2015, which claims the benefit of U.S. Provisional Patent Application No. 62/042,099, filed Aug. 26, 2014, the disclosures of which are incorporated by reference in their entirety herein.

BACKGROUND OF THE INVENTION

In International Patent Application No. PCT/US2014/018175 (WO 2014/130987), the disclosure of which is incorporated by reference in its entirety herein, processes are described for the oxidation of a hydrocarbon such as an alkane with an oxidizing electrophile comprising a main group element in an acidic medium. Processes for use of an oxidizing electrophile in an acidic medium for oxidation of heteroalkanes and arenes are described in U.S. Provisional Patent Application Nos. 62/041,270 and 62/042,101, also incorporated by reference in their entireties herein. In the methods of the inventions, a compound (RH), such as an alkane, heteroalkane, or arene, is contacted with an oxidizing electrophile comprising a reactive main group element (e.g., a compound of formula $MX_n$, in which M is the main group element such as thallium, lead, bismuth, antimony, selenium, tellurium, or iodine, in an oxidized form or state, and X is a negatively charged counterion). The reactive main group element in oxidized form, as a salt, is termed an oxidizing electrophile (e.g., a soft oxidizing electrophile).

Without wishing to be bound by any particular theory, it is believed that this reaction generates a reactive organometallic intermediate ($RMX_{(n-1)}$), which in at least some embodiments is derived from electrophilic substitution of a carbon-bonded hydrogen atom of an $sp^3$- or $sp^2$-hybridized carbon atom by the reactive main group element. The reactive organometallic intermediate, wherein a newly formed bond exists between the hydrocarbyl group and the main group element, can then further react, such as with an oxygen acid like a carboxylic acid, to yield a functionalized hydrocarbon, e.g., a hydrocarbyl ester of the carboxylic acid. Thus, the overall reaction is replacement of a hydrogen atom of a C—H bond of the compound with a functional group, such as an ester group. The byproduct of the oxidizing electrophile, termed an electrophile reduction product, comprises the main group element M in a lower oxidation state relative to the oxidation state of the main group element in the reactive oxidizing electrophile.

In an embodiment, the reaction is carried out in an acidic medium, which yields the reaction product and an electrophile reduction product from the reactive organometallic intermediate, wherein the main group element M has undergone a reduction reaction to a lower oxidation state and the substrate has been transformed to a functionalized (e.g., an oxidized) hydrocarbon. In some embodiments, the reaction product (i.e., the oxidation product) is an oxygenate of the starting compound, such as an alcohol, ketone, aldehyde, ester, or carboxylic acid.

When the acidic medium comprises a carboxylic acid (e.g., acetic acid, trifluoroacetic acid, or the like), the oxidation product must be separated from the acidic medium and from the electrophile reduction product. The electrophile reduction product can be recycled by an oxidative step back to the oxidizing electrophile, and the components of the acidic medium can be recycled back into the reaction milieu. However, the oxidation product needs to be economically recovered in sufficiently pure form in order to provide an efficient and/or cost-effective process for the overall functionalization (e.g., oxidation) reaction.

BRIEF SUMMARY OF THE INVENTION

The invention provides a process for recovery of a functionalized compound reaction product comprising
contacting (i) an oxidizing electrophile comprising a main group element, and (ii) a compound comprising at least one C—H bond, in an acidic medium to form a reaction milieu comprising a functionalized compound reaction product,
contacting the reaction milieu with a water-immiscible organic solvent,
separating the water-immiscible organic solvent from the reaction milieu, wherein the functionalized compound reaction product is dissolved in the water-immiscible organic solvent, and
separating the functionalized compound reaction product and the water-immiscible organic solvent to recover the functionalized compound reaction product.

DETAILED DESCRIPTION OF THE INVENTION

The invention related to a process for recovery of a functionalized compound reaction product comprising
contacting (i) an oxidizing electrophile comprising a main group element, and (ii) a compound comprising at least one C—H bond, in an acidic medium to form a reaction milieu comprising a functionalized compound reaction product,
contacting the reaction milieu with a water-immiscible organic solvent,
separating the water-immiscible organic solvent from the reaction milieu, wherein the functionalized compound reaction product is dissolved in the water-immiscible organic solvent, and
separating the functionalized compound reaction product and the water-immiscible organic solvent.

In the process, the compound comprising at least one C—H bond, i.e., the compound to be functionalized, is an alkane, a heteroalkane, or an arene, as described herein.

An "alkane" is a compound that includes at least one $sp^3$-hybridized carbon atom, in which at least one substituent of that carbon atom is a hydrogen atom such that a C—H bond is present. The alkane can be a straight-chain or branched alkane containing from, for example, from about 1 to about 16 carbon atoms (e.g., from about 1 to about 12 carbon atoms, from about 1 to about 10 carbon atoms, from about 1 to about 8 carbon atoms, from about 1 to about 6 carbon atoms, or from about 1 to about 4 carbon atoms). Examples of alkyl group include methane, ethane, n-propane, isopropane, n-butane, sec-butane, isobutane, tert-butane, n-pentane, isopentane, n-hexane, and the like.

A "heteroalkane" is a compound that includes at least one $sp^3$-hybridized carbon atom, in which at least one substituent of that carbon atom is a hydrogen atom such that a C—H bond is present. The alkane portion of the heteroalkane implies a straight-chain or branched alkyl substituent containing from, for example, from about 1 to about 16 carbon atoms (e.g., from about 1 to about 12 carbon atoms, from about 1 to about 10 carbon atoms, from about 1 to about 8 carbon atoms, from about 1 to about 6 carbon atoms, or from about 1 to about 4 carbon atoms). The heteroalkane additionally comprises at least one "heteroatom," i.e., an atom that is not a carbon or a hydrogen. Examples of heteroatoms include atoms of elements such as oxygen, sulfur, nitrogen, a halogen (e.g., chlorine), and/or a metal (e.g., tin). Thus, a heteroalkane substrate as the term is used herein can be, for example, an alkylcarbinol, an alkylamine, an alkylthiol, a halocarbon, or an organometallic compound. Examples of heteroalkane substrates useful for practice of a method of the invention include alcohols (e.g., n-propanol or n-butanol) and compounds comprising an ether oxygen, an ester, or an amide group. For instance, a method of the invention can be used to provide reaction products of heteroalkanes such as butanol, halobutanes, and butanoyl compounds, such as esters and amides.

An "arene," as the term is used herein, refers to an organic compound comprising at least one $sp^2$-hybridized carbon atom bearing a hydrogen atom, in which the arene compound can further comprise (i) one or more $sp^3$-hybridized carbon atoms, (ii) one or more heteroatoms, or (iii) both (i) and (ii). The term "arene" encompasses "aryl" and "heteroaryl" ring systems.

The term "aryl" refers to an unsubstituted or substituted aromatic carbocyclic moiety, as commonly understood in the art, and includes monocyclic and polycyclic aromatics such as, for example, benzene, biphenyl, naphthalene, anthracene, pyrene, and the like. An aryl moiety generally contains from, for example, 6 to 30 carbon atoms, from 6 to 18 carbon atoms, from 6 to 14 carbon atoms, or from 6 to 10 carbon atoms. It is understood that the term aryl includes carbocyclic moieties that are planar and comprise $4n+2$ $\pi$ electrons, according to Hückel's Rule, wherein $n=1, 2,$ or $3$. The aryl can be substituted or unsubstituted, as described herein.

The term "heteroaryl" refers to aromatic 5 or 6 membered monocyclic groups, 9 or 10 membered bicyclic groups, and 11 to 14 membered tricyclic groups which have at least one heteroatom (O, S, or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups can contain only carbon atoms and can be saturated, partially saturated, or unsaturated. The nitrogen and sulfur atoms can optionally be oxidized, and the nitrogen atoms can optionally be quaternized. Heteroaryl groups which are bicyclic or tricyclic must include at least one fully aromatic ring but the other fused ring or rings can be aromatic or non-aromatic. The heteroaryl group can be attached at any available nitrogen or carbon atom of any ring. Illustrative examples of heteroaryl groups are quinoline, pyridine, pyridazine, pyrimidine, pyrazine, benzimidazole, triazine, imidazole, (1,2,3)- and (1,2,4)-triazole, pyrazine, tetrazole, furan, pyrrole, thiophene, isothiazole, thiazole, isoxazole, and oxadiazole. The heteroaryl can be substituted or unsubstituted, as described herein.

Examples of suitable arene substrates include aryls, such as benzene, phenols, phenolic ethers, derivatives of anilines, haloaryl compounds, naphthalene, and the like. Further examples of suitable arene substrates include heteroaryls, such as pyridine, quinoline, pyrrole, indole, thiophene, and the like. In an embodiment, the arene is benzene, pyridine, quinoline, or naphthalene, each of which is optionally substituted.

A substituted arene typically comprises at least one substituent (e.g., 1, 2, 3, 4, 5, 6, etc.) in any suitable position (e.g., 1-, 2-, 3-, 4-, 5-, or 6-position, etc.). Suitable substituents include, e.g., halo, alkyl, alkenyl, alkynyl, hydroxy, nitro, cyano, amino, alkylamino, alkoxy, aryloxy, aralkoxy, carboxyl, carboxyalkyl, carboxyalkyloxy, amido, alkylamido, haloalkylamido, aryl, heteroaryl, and heterocycloalkyl. In an embodiment, the arene can be substituted with one or more heteroatoms and/or one or more alkyl groups. Examples of heteroatoms include atoms of elements such as oxygen, nitrogen, sulfur, a halogen (e.g., chlorine), and/or a metal (e.g., tin), e.g., aryl or heteroaryl alcohols (phenols), thiols, alkoxys, esters, halocarbons, carboxylic acids, and carboxamides.

In some embodiments, the compound comprising at least one C—H bond is an alkane. Preferably the alkane is methane, ethane, propane, butane, or a mixture thereof. Preferably the alkane is propane or butane. In other embodiments, the compound comprising at least one C—H bond is a heteroalkane. Preferably the heteroalkane is an alcohol. In a particular embodiment, the compound is n-butanol or n-propanol. In still other embodiments, the compound comprising at least one C—H bond is an arene, such as an aryl ring system (e.g., benzene or toluene) or a heteroaryl ring system.

In an embodiment of the process, the functionalized compound reaction product is an oxidation reaction product, such as, for example, an ester or a diester. For example, when the starting compound with at least one C—H bond is propane, a suitable oxidation reaction product is 1,2-propanediol diacetate.

The oxidizing electrophile of any of the methods described herein comprises a main group element. A main group element, as the term is used herein, refers to metals and non-metals, including elements of CAS groups IIIA, IVA, VA, VIA, and VIIA, that are post-transition elements, i.e., being of higher atomic number than the last element of the first transition series, Zn, i.e., of atomic number >30. In an embodiment, the main group element is an element selected from CAS groups IIIA, IVA, VA, and VIA. Thus, an oxidizing electrophile used in practice of methods of the invention includes elements having stable isotopic forms of atomic numbers 31-35, 49-53, and 81-83. In a preferred embodiment, the oxidizing electrophile includes at least one element that is a stable isotopic form of any one of atomic numbers 31-34, 49-52, and 81-83. The main group element, in some embodiments, has a $d^{10}$ electronic configuration. However, an oxidizing electrophile used in practice of a method of the invention can have other than a $d^{10}$ electronic configuration. The main group element can cycle between a higher oxidation state (in the oxidizing electrophile reagent that reacts with the alkane C—H bond) and a lower oxidation state (an electrophile reduction product, from which the oxidizing electrophile can be regenerated, either in situ or in a discrete step). By this means, an economically and environmentally favorable self-contained system for alkane, heteroalkane, or arene conversion, e.g., to alkane, heteroalkane, or arene oxygenates, respectively, can be formed, consuming only a second oxidant (e.g., a peroxide such as hydrogen peroxide, oxygen, ozone, nitric acid, or a halogen such as chlorine). In an embodiment, the main group element in oxidized form is in an oxidation state of $+n$. In other embodiments, the main group element is in an oxidation state of $+(n-2)$ or $+(n-1)$ for an electrophile reduction product that is formed by the oxidizing electrophile.

As known in the art, an oxidizing electrophile can be known as a soft oxidizing electrophile. A "soft" electrophile, as the term is used herein, relates to classification under the hard/soft acid/base (HSAB) concept, known as the Pearson acid base concept, which assigns the terms "hard" or "soft" and the terms "acid" or "base" to chemical species. The term "hard" applies to species that are weakly polarizable, whereas the term "soft" applies to species that are strongly polarizable. See R. G. Pearson, Chemical Hardness—Applications From Molecules to Solids, Wiley-VCH, Weinheim, 1997.

Table 1 is a listing of exemplary species based on Pearson hard and soft theory. Oxidizing electrophiles used in practice of methods of the invention are classified as soft according to the HSAB theory, and include forms of main group elements such as Tl, Pb, Bi, Sb, Se, Te, and I. Higher oxidation states of these elements, as salts or compounds thereof, are used as the soft oxidizing electrophiles for practice of methods of the invention.

TABLE 1

Classification of Pearson Hard and Soft Acids

| Hard Acids | Borderline Acids | Soft Acids |
|---|---|---|
| $H^+$, $Li^+$, $Na^+$, $K^+$, $Be^{+2}$, $Mg^{+2}$, $Ca^{+2}$, $Ba^{+2}$, $Sc^{+3}$, $La^{+2}$, $Ce^{+4}$, $Gd^{+3}$, $Lu^{+3}$, $Th^{+4}$, $U^{+4}$, $UO_2^{+2}$, $Ti^{+4}$, $Zr^{+4}$, $Hf^{+4}$, $VO^{+2}$, $Cr^{+3}$, $BF_3$, $BCl_3$, $Al^{+3}$, $AlCl_3$, $CO_2$, $RCO^+$, $NC^+$, $Si^{+4}$, $Sn^{+4}$ | $Fe^{+2}$, $Co^{+2}$, $Ni^{+2}$, $Zn^{+2}$, $Rh^{+3}$, $Ir^{+3}$, $Ru^{+3}$, $Os^{+3}$, $B(CH_3)_3$, $GaH_3$, $R_3C+$, $C_4H_5+$, $Sn^{+2}$, $Pb^{+2}$, $NO^+$, $Sb^{+3}$, $Bi^{+3}$, $SO_2$ | $Pd^{+2}$, $Pt^{+2}$, $Pt^{+4}$, $Cu^+$, $Ag^+$, $Au^+$, $Cd^{+2}$, $Hg^+$, $Hg^{+2}$, $Tl^{+3}$, $Ph^{+4}$, $Bi^{+5}$, $Br^+$, $Br_2$, $I^+$, $I_2$, $Se^{+6}$, $Te^{+6}$, $I^{+3}$ |

Other soft acids are known to those of skill in the art, and elements having suitable pairs of oxidation states can be selected by the person of skill in the art for practicing the methods of the invention.

In some embodiments, the oxidizing electrophile comprises a main group element selected from thallium, lead, bismuth, antimony, selenium, tellurium, iodine, and a mixture thereof, each of which is in oxidized form. In a particular embodiment, the oxidizing electrophile comprises a main group element selected from thallium, lead, bismuth, antimony, selenium, tellurium, and a mixture thereof, each of which is in oxidized form. In the case of Hg, Tl, and Pb the oxidized forms that are most active are those that have the electronic configuration of Xe, $5d^{10}$, $6s^0$. However, this need not be the electronic configuration of systems that react since I(III), with an electronic configuration of Kr, $4d^{10}$, $5s^2$, $5p^2$, is found to be active for C—H activation. In particular embodiments, the oxidizing electrophile can comprise thallium(III), lead(IV), bismuth(V), iodine(III), Sb(V), iodine (V), or a mixture of any of the foregoing elements. In a preferred embodiment, the oxidizing electrophile comprises thallium(III), lead(IV), bismuth(V), Sb(V), or any mixture thereof. In an embodiment, the oxidizing electrophile comprises thallium(III). In another embodiment, the oxidizing electrophile comprises lead(IV). In yet another embodiment, the oxidizing electrophile comprises bismuth(V). In still yet another embodiment, the oxidizing electrophile comprises Sb(V).

In some embodiments, the oxidizing electrophile comprising a main group element in oxidized form is a salt, wherein the counterion of the main group element in oxidized form is a conjugate anion of an acid (e.g., one or more trifluoroacetate, acetate, sulfate, and/or alkylsulfonate anions). For example, the oxidizing electrophile can have the formula $M^{+n}X_n$, in which M is a metal or non-metal main group element cation in an oxidation state of n, X is an anionic counterion, and n is the number of anionic charges necessary to balance the n+ positive charge of the metal ion. The anionic counterion (X) is any suitable anionic counterion/ligand, including one or more trifluoroacetate, acetate, sulfate, and/or alkylsulfonate anions.

In an embodiment of any of the processes described herein, the reaction of (i) the oxidizing electrophile comprising a main group element, and (ii) a compound comprising at least one C—H bond is carried out in an acidic medium, including an aqueous acidic medium. The acidic acid is any suitable acid, such as a mineral acid, a carboxylic acid, a sulfonic acid, aqueous solutions thereof, or any combination thereof. In some embodiments, the acidic medium comprises an aqueous carboxylic acid (e.g., formic acid, acetic acid, butyric acid, caproic acid, trifluoracetic acid). Preferably the carboxylic acid is acetic acid or trifluoroacetic acid.

The acidic medium further comprises a water-immiscible organic solvent. The water-immiscible organic solvent is any suitable solvent that undergoes phase separation from an aqueous media under processing conditions (e.g., at room temperature or at an elevated temperature, such as greater than 30° C., greater than 40° C., greater than 50° C., greater than 60° C., greater than 70° C., greater than 80° C., greater than 90° C., or greater than 100° C.) such that the water-immiscible organic solvent acts as an extraction solvent. In some embodiments, the water-immiscible organic solvent comprises a hydrocarbon solvent, an oxycarbon solvent, or a mixture thereof. In other embodiments, the extraction solvent comprises a mixture of two or more solvents, such as a mixture of straight chain hydrocarbons, branched chain hydrocarbons, cycloalkyl hydrocarbons, aryl hydrocarbons, arylalkyl hydrocarbons, and/or oxycarbons.

The hydrocarbon solvent comprises a straight chain, branched chain, or cyclic hydrocarbon, or a mixture thereof. In some embodiments, the hydrocarbon solvent comprises a straight chain hydrocarbon comprising 2 to about 20 carbon atoms (e.g., 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms or any range thereof). For example, the hydrocarbon solvent can be propane, butane, pentane, hexane, heptane, dodecane, octadecene, or ligroin, or a mixture thereof. Preferably the straight chain hydrocarbon is propane, n-butane, or n-pentane, or a mixture thereof. In some embodiments, the hydrocarbon solvent is a branched chain hydrocarbon comprising 4 to about 20 carbon atoms (e.g., 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms or any range thereof). Preferably the branched chain hydrocarbon is isobutane, isopentane, or tert-pentane, or a mixture thereof. In some embodiments, the hydrocarbon solvent comprises a cyclic hydrocarbon comprising between 3 and about 20 carbon atoms (e.g., 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms or any range thereof). Examples of a cyclic hydrocarbon include cyclopentane, cyclohexane, cyclohexene, methylcyclohexane, cycloheptane, and cyclooctane. In other embodiments, the extraction solvent comprises an aryl or arylalkyl hydrocarbon, containing between 6 and about 20 carbon atoms (e.g., 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms or any range thereof). Examples of an aryl or arylalkyl hydrocarbon include benzene, toluene, xylenes, pentamethylbenzene, tetramethylbenzene (durene), limonene, and the like.

An oxycarbon solvent is any hydrocarbon comprising one or more oxygen atoms, such as an ether, an ester, a ketone, or a carboxylic acid comprising between 4 and about 20 carbon atoms (e.g., 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms or any range thereof). Examples of an oxycarbon solvent include diethyl ether, diisopropyl ether, di-t-butyl ether, methyl t-butyl ether, ethyl t-butyl ether, methoxyethane, dimethoxyethane, dimethoxymethane, 1,4-dioxane, morpholine, diethylene glycol diethyl ether, diglyme, tetrahydrofuran, tetrahydropyran, ethyl acetate, methyl acetate, methoxypropyl acetate, n-butyl acetate, methanol, ethanol, n-propanol, i-propanol, 1,3-propanediol, n-butanol, 2-butanol, i-butanol, t-butyl alcohol, 1,4-butanediol, 1,2,4-butanetriol, 2-methyl-1butanol, 3-methyl-2-butanol, 2-methyl-1-pentanol, 2-pentanol, neopentyl alcohol, tert-amyl alcohol, 2-ethylhexanol, glycerol, ethylene glycol, diethylene glycol, propylene glycol, benzyl alcohol, and the like.

The result of the separation step using the water-immiscible organic solvent is an aqueous acidic medium containing main group metal salts, i.e., the electrophile reduction product depleted in oxygenation product, and an extraction solvent solution containing the desired oxidation product.

The oxidation product that is extracted from the reaction mixture by use of the water-immiscible organic solvent (e.g., a hydrocarbon and/or oxycarbon solvent) can be recovered from the extraction solution by distillation, such as simple distillation or fractional distillation, or by other suitable separation methods (e.g., decantation, evaporation, or chromatography). The oxidation product of the reaction can have a lower or a higher boiling point than the water-immiscible organic solvent. In an embodiment, the functionalized compound reaction product has a higher boiling point than the acidic medium.

The aqueous phase of the reaction milieu following solvent extraction of the reaction mixture can contain residual amounts of the immiscible organic solvent (extraction solvent) after phase separation. The residual immiscible organic solvent can be removed by further extraction with the reactant compound comprising at least one C—H bond leading to an aqueous acidic medium substantially free from the extraction solvent. An aqueous acidic medium that is substantially free from the extraction solvent contains, for example, less than 20% by volume of the extraction solvent (e.g., less than 15% by volume, less than 10% by volume, less than 5% by volume, less than 2% by volume, or less than 1% by volume).

In an embodiment of any of the processes described herein, the water-immiscible extraction solvent is the same as the compound comprising as least one C—H bond. For example, the compound comprising at least one C—H bond and the water-immiscible extraction solvent can both be propane or n-butane. For instance, propane in the reaction with the oxidizing electrophile in an aqueous carboxylic acid medium can yield a mixture of propanol and propanediol esters. More specifically, if the carboxylic acid medium comprises acetic acid, 1,2-propanediol diacetate can be the reaction product. This reaction product can be removed from the reaction milieu by extraction with liquid propane, i.e., under pressure. Next, the liquid propane extraction solvent and 1,2-propanediol diacetate can be separated by fractional distillation to provide the 1,2-propanediol diacetate substantially free of acetic acid and main group metal acetate salts.

By the use of the extraction process as disclosed and claimed herein, a more economically advantageous method for recovery of the valuable functionalized compound reaction products, such as the esters exemplified above, can be achieved. There are advantages to use of the extraction process as disclosed herein relative to simple distillation of the solvent milieu that contains a desired product. For instance, the reaction products may be less volatile than the acidic reaction medium (e.g., carboxylic acid), in which case high energy costs would be incurred by the need to distill away the acid medium (e.g., carboxylic acid) before recovering the reaction product. By use of a method of the invention, a higher-boiling oxidation product from the reaction can be first separated from the acid medium (e.g., carboxylic acid), and from the electrophile reduction product (inorganic salts), prior to recovery from the extraction solvent, minimizing the need to distill the acid reaction solvent and avoiding potential overheating and formation of thermal by-products. Moreover, in an embodiment, all three steps, i.e., (i) contacting an oxidizing electrophile comprising a main group element and a compound comprising at least one C—H bond in an acidic medium, preferably comprising an aqueous carboxylic acid, (ii) contacting the reaction milieu with a water-immiscible organic solvent, and (iii) separating the water-immiscible organic solvent can be carried out as a continuous process.

The invention is further illustrated by the following embodiments.

(1) A process for recovery of a functionalized compound reaction product comprising contacting (i) an oxidizing electrophile comprising a main group element, and (ii) a compound comprising at least one C—H bond, in an acidic medium to form a reaction milieu comprising a functionalized compound reaction product, contacting the reaction milieu with a water-immiscible organic solvent, separating the water-immiscible organic solvent from the reaction milieu, wherein the functionalized compound reaction product is dissolved in the water-immiscible organic solvent, and separating the functionalized compound reaction product and the water-immiscible organic solvent.

(2) The process of embodiment (1), wherein the compound comprising at least one C—H bond is an alkane, a heteroalkane, or an arene, wherein the heteroalkane comprises at least one $sp^3$-hybridized carbon atom bearing a hydrogen atom and at least one heteroatom other than a carbon or hydrogen atom, and the arene comprises at least one sp²-hybridized carbon atom bearing a hydrogen.

(3) The process of embodiment (2), wherein the compound comprising at least one C—H bond is an alkane, preferably methane, ethane, propane, butane, or a mixture thereof.

(4) The process of embodiment (2), wherein the compound comprising at least one C—H bond is a heteroalkane, preferably an alcohol.

(5) The process of embodiment (2), wherein the compound comprising at least one C—H bond is an arene, preferably an aryl ring system or a heteroaryl ring system.

(6) The process of any one of embodiments (1)-(5), wherein the acidic medium comprises an aqueous carboxylic acid, preferably acetic acid or trifluoroacetic acid (7) The process of any one of embodiments (1)-(6), wherein the functionalized compound reaction product is an oxidation reaction product.

(8) The process of embodiment (7), wherein the oxidation reaction product is an ester or a diester.

(9) The process of embodiment (8), wherein the hydrocarbon is propane and the hydrocarbon oxidation reaction product is 1,2-propanediol diacetate.

(10) The process of any one of embodiments (1)-(9), wherein the water-immiscible organic solvent is a hydrocarbon solvent, an oxycarbon solvent, or a mixture thereof.

(11) The process of embodiment (10), wherein the hydrocarbon solvent is a straight chain, branched chain, or cyclic hydrocarbon, or a mixture thereof.

(12) The process of embodiment (11), wherein the straight chain hydrocarbon comprises 2 to about 20 carbon atoms.

(13) The process of embodiment (12), wherein the straight chain hydrocarbon is propane, n-butane, or n-pentane.

(14) The process of embodiment (11), wherein the branched chain hydrocarbon comprises 4 to about 20 carbon atoms.

(15) The process of embodiment (14), wherein the branched chain hydrocarbon is isobutane, isopentane, or tert-pentane.

(16) The process of any one of embodiments (1)-(15), wherein the water-immiscible extraction solvent is the same as the compound comprising as least one C—H bond.

(17) The process of embodiment (16), wherein the compound comprising at least one C—H bond and the water-immiscible extraction solvent are both propane.

(18) The process of embodiment (16), wherein the compound comprising at least one C—H bond and the water-immiscible extraction solvent are both n-butane.

(19) The process of any one of embodiments (1)-(18), wherein the functionalized compound reaction product and the water-immiscible organic solvent are separated by distillation.

(20) The process of any one of embodiments (1)-(19), wherein the functionalized compound reaction product has a higher boiling point than the acidic medium.

(21) The process of any one of embodiments (1)-(20), wherein (i) contacting an oxidizing electrophile comprising a main group element and a compound comprising at least one C—H bond in an acidic medium, preferably comprising an aqueous carboxylic acid, (ii) contacting the reaction milieu with a water-immiscible organic solvent, and (iii) separating the water-immiscible organic solvent are all carried out as a continuous process.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for recovery of a functionalized compound reaction product that is soluble in a water-immiscible organic solvent comprising contacting (i) an oxidizing electrophile comprising a main group element selected from the group consisting of thallium, lead, bismuth, antimony, selenium, arsenic, tellurium, and a mixture thereof, and (ii) a compound comprising at least one C—H bond that is an alkane, a heteroalkane, or an arene, in an aqueous acidic medium to form a reaction milieu comprising a reaction product that is an alkane oxygenate, heteroalkane oxygenate, or arene oxygenate, respectively, wherein at least one C—H bond of the starting alkane, heteroalkane, or arene compound comprising at least one C—H bond is replaced with an oxygenate group, and wherein the reaction product is soluble in a water-immiscible organic solvent, contacting the reaction milieu with a water-immiscible organic solvent that is a hydrocarbon solvent in which the reaction product is soluble, separating the water-immiscible organic solvent from the reaction milieu, wherein the reaction product is dissolved in the water-immiscible organic solvent, and separating the reaction product and the water-immiscible organic solvent.

2. The process of claim 1, wherein the compound comprising at least one C—H bond is an alkane.

3. The process of claim 2, wherein the alkane is selected from the group consisting of methane, ethane, propane, butane, and a mixture thereof.

4. The process of claim 1, wherein the compound comprising at least one C—H bond is a heteroalkane that is an alcohol.

5. The process of claim 1, wherein the compound comprising at least one C—H bond is an arene that is an aryl ring system or a heteroaryl ring system.

6. The process of claim 1, wherein the aqueous acidic medium comprises an aqueous carboxylic acid.

7. The process of claim 1, wherein the reaction product is an ester or a diester.

8. The process of claim 7, wherein the compound comprising at least one C—H bond is propane and the reaction product is 1,2-propanediol diacetate.

9. The process of claim 1, wherein the hydrocarbon solvent is a straight chain, branched chain, or cyclic hydrocarbon, or a mixture thereof.

10. The process of claim 9, wherein the hydrocarbon solvent is a straight chain hydrocarbon comprising 2 to about 20 carbon atoms.

11. The process of claim 10, wherein the straight chain hydrocarbon is propane, n-butane, or n-pentane.

12. The process of claim 9, wherein the hydrocarbon solvent is a branched chain hydrocarbon comprising 4 to about 20 carbon atoms.

13. The process of claim 12, wherein the branched chain hydrocarbon is isobutane, isopentane, or tert-pentane.

14. The process of claim 1, wherein the water-immiscible organic solvent used for separating the reaction product is the same as the compound comprising as least one C—H bond.

15. The process of claim 14, wherein the compound comprising at least one C—H bond and the water-immiscible organic solvent are both propane or n-butane.

16. The process of claim 1, wherein the reaction product and the water-immiscible organic solvent are separated by distillation.

17. The process of claim 1, wherein the reaction product has a higher boiling point than the aqueous acidic medium.

18. The process of claim 1, wherein (i) contacting the oxidizing electrophile comprising a main group element and the compound comprising at least one C—H bond in the aqueous acidic medium, (ii) contacting the reaction milieu with the water-immiscible organic solvent, and (iii) separating the water-immiscible organic solvent from the reaction milieu are all carried out as a continuous process.

19. The process of claim 1, wherein the oxidizing electrophile comprises a main group element selected from the group consisting of lead, bismuth, antimony, selenium, arsenic, tellurium, and a mixture thereof.

* * * * *

UNITED STATES PATENT AND TRADEMARK OFFICE
CERTIFICATE OF CORRECTION

PATENT NO. : 10,654,790 B2
APPLICATION NO. : 15/506611
DATED : May 19, 2020
INVENTOR(S) : Kouba et al.

Page 1 of 1

It is certified that error appears in the above-identified patent and that said Letters Patent is hereby corrected as shown below:

In the Specification

Column 1, at Line 14, please insert the following paragraph:
-- STATEMENT OF GOVERNMENT LICENSE RIGHTS
This invention was made with government support under grant number GQI0044-133945 awarded by the United States Department of Energy. The government has certain rights in the invention. --

Signed and Sealed this
Fourth Day of August, 2020

Andrei Iancu
*Director of the United States Patent and Trademark Office*